United States Patent
Thompson

[19]

[11] Patent Number: 6,165,211
[45] Date of Patent: Dec. 26, 2000

[54] EXPANDABLE STENT-GRAFT COVERED WITH EXPANDED POLYTETRAFLUOROETHYLENE

[75] Inventor: Paul J. Thompson, New Hope, Minn.

[73] Assignee: Schneider (USA) Inc., Plymouth, Minn.

[21] Appl. No.: 08/988,725

[22] Filed: Dec. 11, 1997

Related U.S. Application Data

[62] Division of application No. 08/751,884, Nov. 18, 1996, Pat. No. 5,788,626.
[60] Provisional application No. 60/007,435, Nov. 21, 1995.

[51] Int. Cl.$^7$ ............................................. A61F 2/06
[52] U.S. Cl. ........................... 623/1.13; 623/1.39; 623/12
[58] Field of Search ......................... 623/1, 12, 1.12, 623/1.13, 1.28, 1.29, 1.39; 600/36

[56] References Cited

U.S. PATENT DOCUMENTS

| | | | |
|---|---|---|---|
| 3,953,566 | 4/1976 | Gore | 264/288 |
| 4,482,516 | 11/1984 | Bowman et al. | 264/127 |
| 4,655,771 | 4/1987 | Wallsten | 623/1 |
| 4,850,999 | 7/1989 | Planck | 623/1 |
| 4,954,126 | 9/1990 | Wallsten | 600/36 |
| 5,061,275 | 10/1991 | Wallsten et al. | 623/1 |
| 5,064,435 | 11/1991 | Porter | 623/12 |
| 5,071,407 | 12/1991 | Termin et al. | 604/104 |
| 5,112,900 | 5/1992 | Buddenhagen et al. | 524/484 |
| 5,123,917 | 6/1992 | Lee | 623/1 |
| 5,147,385 | 9/1992 | Beck et al. | 623/1 |
| 5,221,261 | 6/1993 | Termin et al. | 604/104 |
| 5,234,456 | 8/1993 | Silvestrini | 606/194 |
| 5,282,823 | 2/1994 | Schwartz et al. | 606/198 |
| 5,282,824 | 2/1994 | Gianturco | 606/198 |
| 5,378,239 | 1/1995 | Termin et al. | 604/104 |
| 5,591,226 | 1/1997 | Trerotola et al. | 623/1 |
| 5,607,468 | 3/1997 | Rogers et al. | 623/1 |
| 5,607,478 | 3/1997 | Lentz et al. | 623/12 |
| 5,609,624 | 3/1997 | Kalis | 623/1 |
| 5,628,782 | 5/1997 | Myers et al. | 623/1 |
| 5,628,786 | 5/1997 | Banas et al. | 623/1 |
| 5,628,788 | 5/1997 | Pinchuk | 623/1 |
| 5,645,559 | 7/1997 | Hachtman et al. | 606/198 |
| 5,667,523 | 9/1997 | Bynon et al. | 623/12 |
| 5,718,973 | 2/1998 | Lewis et al. | 623/1 |
| 5,749,880 | 5/1998 | Banas et al. | 623/12 |
| 5,788,626 | 8/1998 | Thompson | 600/36 |
| 5,843,166 | 12/1998 | Lentz et al. | 623/1 |
| 5,993,489 | 11/1999 | Lewis et al. | 623/12 |

FOREIGN PATENT DOCUMENTS

| | | |
|---|---|---|
| 0551179A1 | 7/1993 | European Pat. Off. . |
| 0621015A1 | 10/1994 | European Pat. Off. . |
| 3918736A1 | 12/1990 | Germany . |
| 8704935 | 8/1987 | WIPO . |
| 9505131 | 2/1995 | WIPO . |
| 9505132 | 2/1995 | WIPO . |
| 9505555 | 2/1995 | WIPO . |
| 9600103 | 1/1996 | WIPO . |
| 9628115 | 9/1996 | WIPO . |
| 9640001 | 12/1996 | WIPO . |
| 9707751 | 3/1997 | WIPO . |

*Primary Examiner*—Paul B. Prebilic
*Attorney, Agent, or Firm*—Hoffmann & Baron, LLP

[57] ABSTRACT

The expandable stent-graft generally defines a cylindrical lumen made from a stent having a discontinuous wall that is at least substantially covered with an expanded polytetrafluoroethylene material. The expanded polytetrafluoroethylene covering may be a biaxially oriented, expanded polytetrafluoroethylene material having nodules and longitudinal and circumferential fibrils or a uniaxially oriented, expanded polytetrafluoroethylene material. The expandable stent-graft expands and compresses in association with the stent structure as it is contracted and expanded.

18 Claims, 6 Drawing Sheets

EXPANDABLE STENT-GRAFT COVERED WITH EXPANDED POLYTETRAFLUOROETHYLENE

This is a division of U.S. application Ser. No. 08/751,884, filed on Nov. 18, 1996 for "Method of Making a Stent-Graft Covered with Expanded Polytetrafluoroethylene" now U.S. Pat. No. 5,788,626, which claims the benefit of U.S. Provisional Application Ser. No. 60/007,435, filed on Nov. 21, 1995, entitled "Expandable Stent Graft Covered with Expanded Polytetrafluoroethylene".

BACKGROUND OF THE INVENTION

The present invention is generally directed to an expandable stent-graft made from a stent covered with expanded polytetrafluoroethylene.

The use of covered expandable stent-grafts for bodily lumen repair is known in the art. Covered expandable stent-grafts may be implanted in a radially compressed state, generally using a catheter, into blood vessels, urinary tracts, biliary tracts, esophageal, femoralpopliteac, venous, iliac, arterial-venus, venus cava, tracheo bronchial, abdominal aorta, thoracic aorta, coronary arteries, carotid arteries, colonic, fallopian, eustachian, ureter, urethra, prostrate or virtually any duct, gorge, or body chamber in a body.

The expandable stent-graft is generally positioned and released from a delivery catheter at a damaged area as desired. Expandable stent-grafts provide outward pressure and support for the body lumen walls, thus creating improved passageways. The addition of a covering on an expandable stent acts to reduce cell growth or occlusions in the interior of the lumen.

Coverings and covered expandable stents that are known in the art are disclosed in the following documents: U.S. Pat. Nos. 3,953,566 to Gore; 4,655,771 to Wallsten; 5,061,275 to Wallsten et al; 5,112,900 to Buddenhagen et al; 5,123,917 to Lee; 5,282,823 to Schwartz et al; 5,282,824 to Gianturco, 4,850,999 to Planck, European Patent Application No. 0 621 015 A1 to Lukic, European Patent Application No. 0 551 179 A1 to Palmaz; DE 3918736-A1 to Vallbracht; Patent Cooperation Treaty Application WO 95/05131 to Gore; Patent Cooperation Treaty Application WO 95/05132 to Gore; Patent Cooperation Treaty Application WO 95/05555 to Gore; Patent Cooperation Treaty Application WO 87/04935 to Fischell. (All documents cited herein, including the foregoing, are incorporated herein in their entireties for all purposes.)

It is an object of the present invention to provide an expandable stent-graft which is covered, at least in part, with expanded polytetrafluoroethylene (ePTFE).

Other objects of the invention will become apparent to those skilled in the art through familiarization with the specification and claims herein.

SUMMARY OF THE INVENTION

The expandable stent-graft of the present invention is designed to provide an expanded polytetrafluoroethylene covering that expands and compresses in association with the stent structure as the stent structure expands and contracts. The expandable stent-graft of the present invention may be used for repair and support of body vessel walls.

In preferred embodiments of the present invention, an expandable stent-graft includes a bonded layer of expanded polytetrafluoroethylene covering a stent so that the longitudinal fibrils of the cover are at least substantially extended to adapt to the stent longitudinal expansion when the stent is radially compressed; circumferential fibrils are at least substantially folded to adapt to the stent radial compression when the stent is longitudinally expanded; longitudinal fibrils are at least substantially folded to adapt to the stent longitudinal compression when the stent is radially expanded; and so the circumferential fibrils are at least substantially extended to adapt to the stent radial expansion when the stent is longitudinally compressed.

In other preferred embodiments of the present invention, an expandable stent-graft includes a bonded layer of expanded polytetrafluoroethylene covering a stent so that the inter-nodule distance measured in the longitudinal direction between nodules is increased when the expandable stent-graft is radially compressed; the inter-nodule distance measured in the longitudinal direction between nodules is decreased when the expandable stent-graft is radially expanded; the inter-nodule distance measured in the circumferential direction between nodules is increased when the expandable stent-graft is longitudinally compressed; and so the inter-nodule distance measured in the circumferential direction between nodules is decreased when the expandable stent-graft is longitudinally expanded.

In sum, the present invention relates to an expandable prosthesis having (a) a discontinuous wall defining a lumen adapted to assume a longitudinally contracted position and a longitudinally expanded position; and (b) at least one layer of expanded polytetrafluoroethylene having a first average longitudinal inter-nodule distance in a free state, the layer of polytetrafluoroethylene affixed to the wall such that it has a second average longitudinal inter-nodule distance when the wall is in the longitudinally contracted position, the second average longitudinal inter-nodule distance being less than the first average longitudinal inter-nodule distance. The layer of expanded polytetrafluoroethylene may have (i) an average longitudinal inter-nodule distance of between about 0 and about 50 microns, preferably between about 5 and about 45 or between about 20 and about 30 microns, when the wall is in the longitudinally contracted position, and (ii) an average longitudinal inter-nodule distance of between about 50 and about 150 microns, preferably between about 60 and about 14 or between about 80 and about 120 microns, when the wall is in the longitudinally expanded position.

The present invention also relates to an expandable prosthesis having (a) a discontinuous wall defining a lumen adapted to assume a radially contracted position and a radially expanded position; and (b) at least one tubular layer of an expanded polytetrafluoroethylene having a first average circumferential inter-nodule distance in a free state, the layer of polytetrafluoroethylene affixed to the wall such that it has a second average circumferential inter-nodule distance when the wall is in the radially contracted state, the second average circumferential inter-nodule distance being less than the first average circumferential inter-nodule distance. The tubular layer of expanded polytetrafluoroethylene may have (i) an average circumferential inter-nodule distance of between about 0 and about 75 microns, preferably between about 5 and about 70 or between about 20 and about 50 microns, when the wall is in the radially contracted position, and (ii) an average circumferential inter-nodule distance of between about 75 and about 150 microns, preferably between about 80 and about 140 microns or between about 80 and about 120 microns, when the wall is in the radially expanded position.

The present invention also relates to an expandable prosthesis having (a) a discontinuous wall generally defining a lumen adapted to assume a longitudinally expanded position and a longitudinally contracted position; and (b) at least one layer of expanded polytetrafluoroethylene having a first average longitudinal inter-nodule distance in a free state, the layer of polytetrafluoroethylene affixed to the wall such that the polytetrafluoroethylene has a second average longitudinal inter-nodule distance between 0 and 99 percent of the first average longitudinal inter-nodule distance when the wall is in the longitudinally contracted position. The second average longitudinal inter-nodule distance may be between about 20 and about 50 percent of the first average longitudinal inter-nodule distance when the wall is in the longitudinally contracted position.

The present invention also relates to an expandable prosthesis having (a) a discontinuous wall generally defining a lumen adapted to assume a radially expanded position and a radially contracted position; and (b) at least one layer of expanded polytetrafluoroethylene having a first average circumferential inter-nodule distance in a free state, the layer of polytetrafluoroethylene affixed to the wall such that the polytetrafluoroethylene has a second average circumferential inter-nodule distance less than about 50 percent of the first average circumferential inter-nodule distance when the wall is in the radially contracted position. The second average circumferential inter-nodule distance may be less than about 25 percent of the first average circumferential inter-nodule distance when the wall is in the radially contracted position.

The present invention also relates to an expandable prosthesis having (a) a discontinuous wall defining a lumen adapted to assume a radially expanded position and a radially contracted position; and (b) at least one layer of expanded polytetrafluoroethylene having a first average longitudinal inter-nodule distance and a first average circumferential inter-nodule distance in a free state, the layer of the polytetrafluoroethylene affixed to the wall such that the polytetrafluoroethylene has a second average longitudinal inter-nodule distance between 0 and 99 percent of the first average longitudinal inter-nodule distance when the wall is in the radially expanded position and a second average circumferential inter-nodule distance less than about 50 percent of the first average circumferential inter-nodule distance when the wall is in the radially contracted position. The second average longitudinal inter-nodule distance may be between about 20 and about 50 percent of the first average longitudinal inter-nodule distance, and the second average circumferential inter-nodule distance may be less than about 25 percent of the first average circumferential inter-nodule distance.

The present invention also relates to an expandable stent-graft having (a) a braided self-expanding stent characterized by a longitudinal shortening upon radial expansion from a first longitudinal stent length to a second longitudinal stent length; and (b) at least one tubular layer of biaxially oriented expanded polytetrafluoroethylene comprising nodules and fibrils affixed to the stent characterized by a shortening of average longitudinal inter-nodule distance upon radial expansion from a first average longitudinal inter-nodule distance to a second average longitudinal inter-nodule distance; wherein the ratio of first longitudinal stent length to second longitudinal stent length is within about 25 percent of, and is preferably substantially the same as, the ratio of first average longitudinal inter-nodule distance to a second average inter-nodule distance. The present invention also relates an expandable stent-graft having (a) a braided self-expanding stent characterized by a longitudinal shortening upon radial expansion; (b) at least one layer of uniaxially oriented expanded polytetrafluoroethylene affixed to the stent, the polytetrafluoroethylene characterized by having substantially no nodules.

The present invention also relates to a method of making an expandable prosthesis including (a) providing a self-expanding braided stent having a longitudinal orientation in an at least partially radially expanded state; (b) providing at least one layer of expanded polytetrafluoroethylene having a longitudinal orientation and a first average longitudinal inter-nodule distance in a free state; (c) longitudinally compressing the layer of expanded polytetrafluoroethylene so that the resulting longitudinally compressed layer has a second average longitudinal inter-nodule distance which is less than the first average longitudinal inter-nodule distance; and (d) affixing the longitudinally compressed layer of expanded polytetrafluoroethylene to the self-expanding braided stent in the at least partially radially expanded state such that the longitudinal orientations of the stent and layer of expanded polytetrafluoroethylene substantially correspond with one another.

BRIEF DESCRIPTION OF THE DRAWINGS

The foregoing features, objects and advantages of the present invention will become apparent to those skilled in the art from the following detailed description of preferred embodiments, especially when considered in conjunction with the accompanying drawings in which:

FIGS. 4–12 illustrates steps of making the expandable stent-graft according to the present invention, wherein:

FIG. 4 depicts a mandrel;

FIG. 5 depicts the biaxially oriented expanded polytetrafluoroethylene (ePTFE) material (tube, sheet or strips or any combination of tube, sheet or strips) at least partially covering the mandrel;

FIG. 6 depicts the ePTFE material being longitudinally compressed onto the mandrel and further illustrates the longitudinal fibrils being substantially folded and the circumferential fibrils allowed to remain substantially extended;

FIG. 7 depicts an expanded stent, having an inside diameter greater than the combined outside diameter of the mandrel and the ePTFE material, being positioned over the longitudinally compressed ePTFE material on the mandrel;

FIG. 8 depicts a section view of the stent over the longitudinally compressed ePTFE material;

FIG. 9 depicts an end view of the stent over the longitudinally compressed ePTFE material;

FIG. 10 depicts an outer layer of longitudinally compressed ePTFE material positioned over the stent, an inner layer of longitudinally compressed ePTFE material and the mandrel;

FIG. 11 depicts a section view of an outer layer of longitudinally compressed ePTFE material positioned over the stent and an inner layer of longitudinally compressed ePTFE material. The ePTFE materials are bonded over or throughout the outside surface, inside surface or throughout the discontinuous wall of the stent;

FIG. 12 depicts an end view of an outer layer of longitudinally compressed ePTFE material positioned over the stent and an inner layer of longitudinally compressed ePTFE material. The ePTFE materials are bonded over or throughout the outside surface, inside surface or throughout the discontinuous wall of the stent;

DESCRIPTION OF THE PREFERRED EMBODIMENTS

Figure 1:
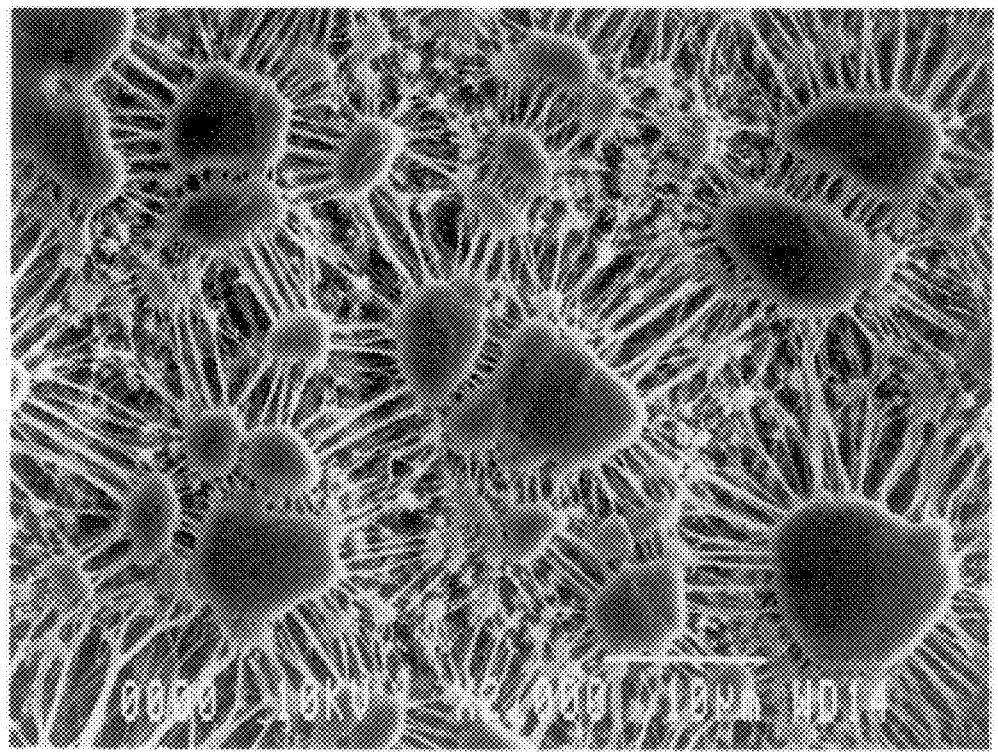
FIG. 1 depicts a micrograph view showing the nodules and fibrils of a biaxially oriented, expanded polytetrafluoroethylene material at a 2000×X magnification.
Figure 2:
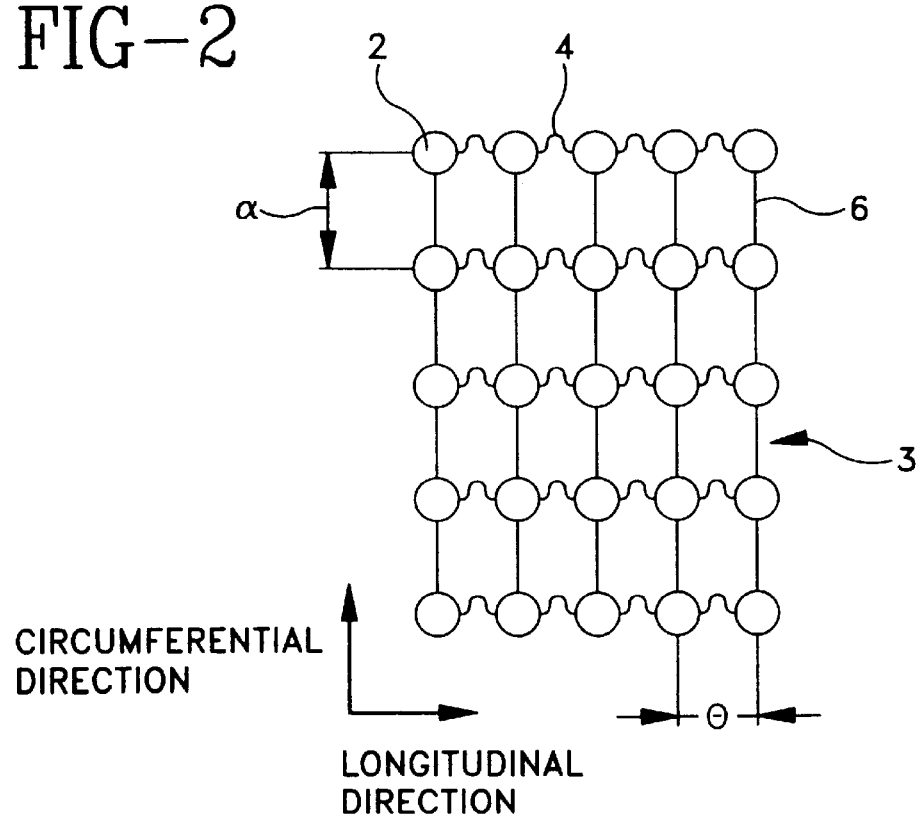
FIG. 2 depicts an illustration of the nodule and fibril relationship and the inter-nodule distances of a biaxially oriented, expanded polytetrafluoroethylene material on a stent that is longitudinally compressed.
Figure 3:
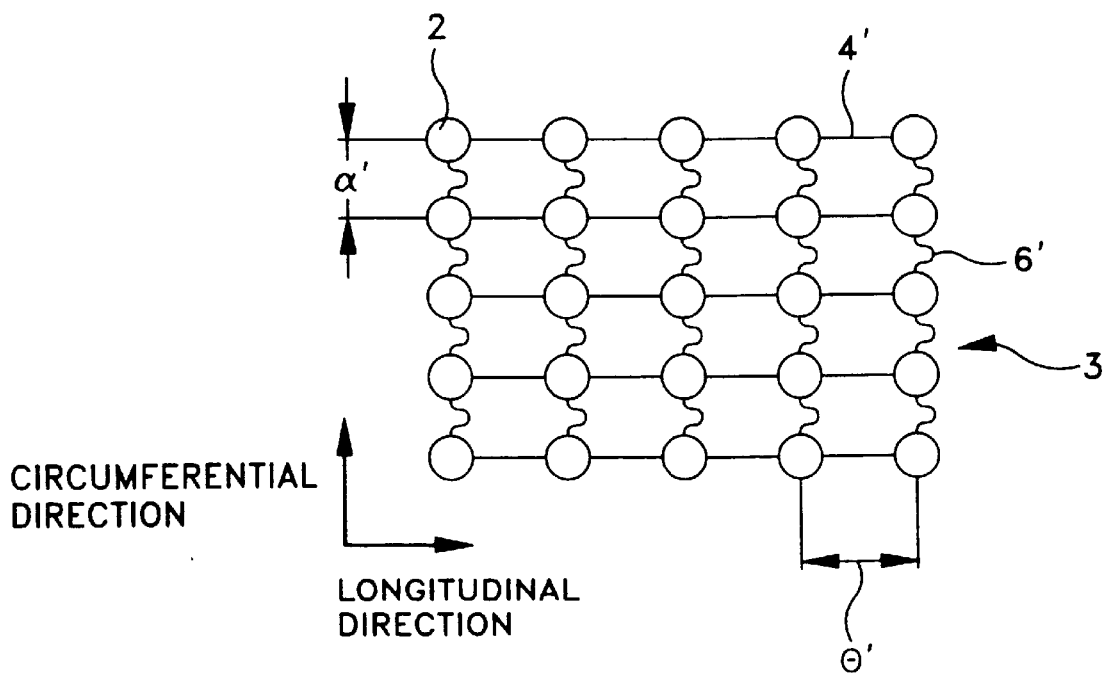
FIG. 3 depicts a view of the nodule and fibril relationship and the inter-nodule distances of a biaxially oriented, expanded polytetrafluoroethylene material on a stent that is radially compressed.
Figure 4:
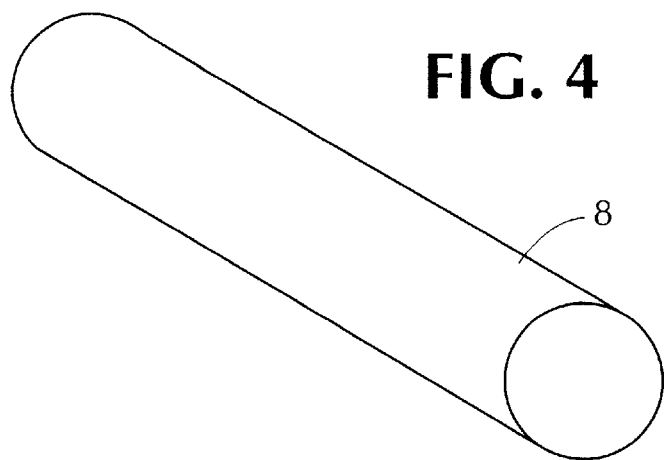
Figure 5:
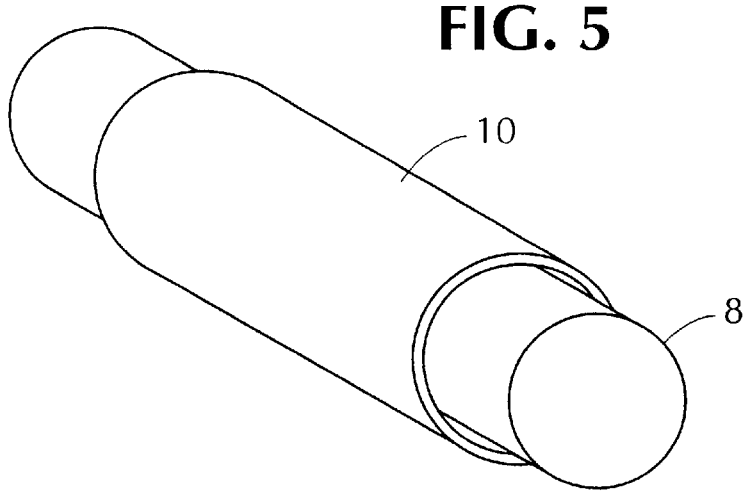
Figure 6:
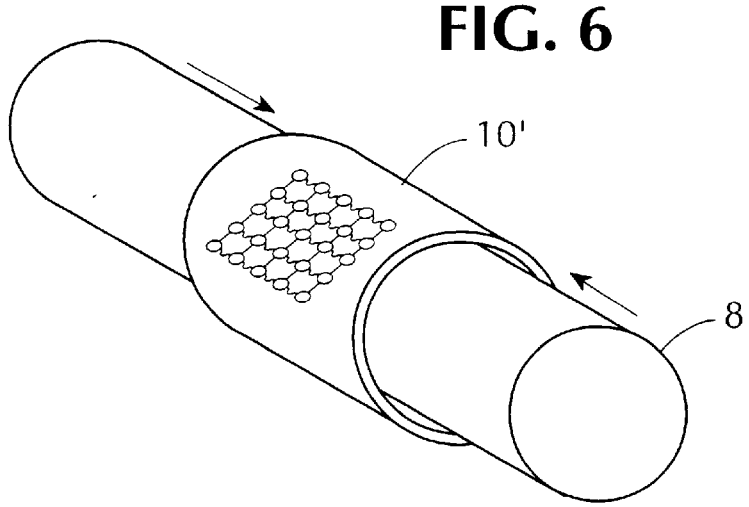
Figure 7:
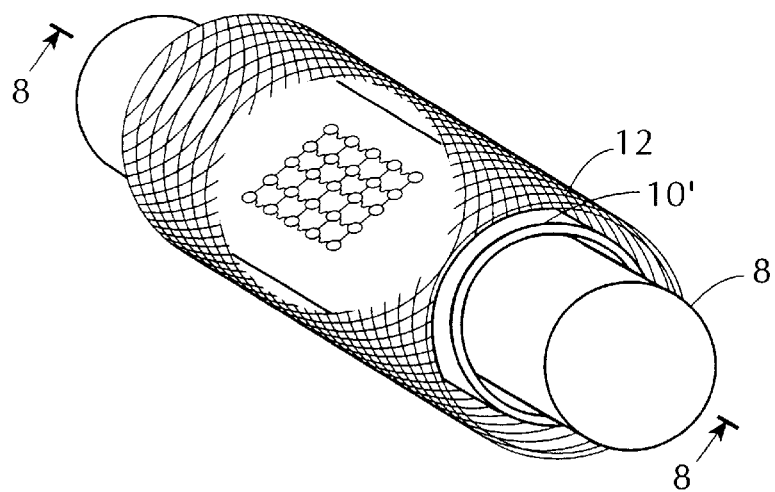
Figure 8:
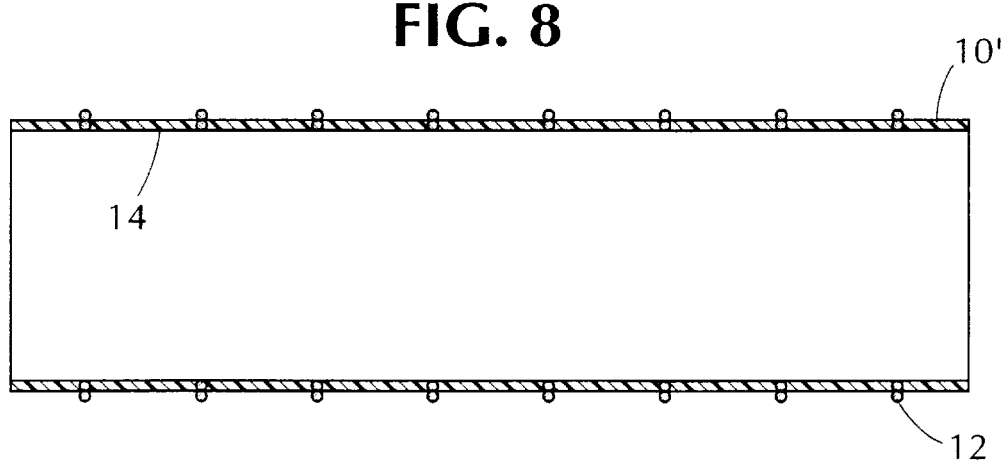
Figure 9:
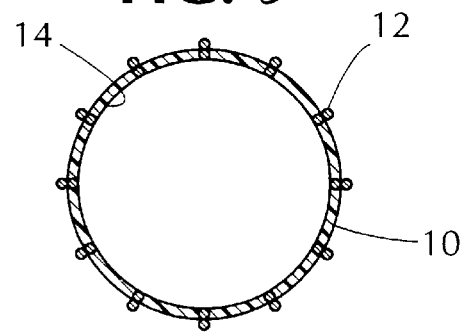
Figure 10:
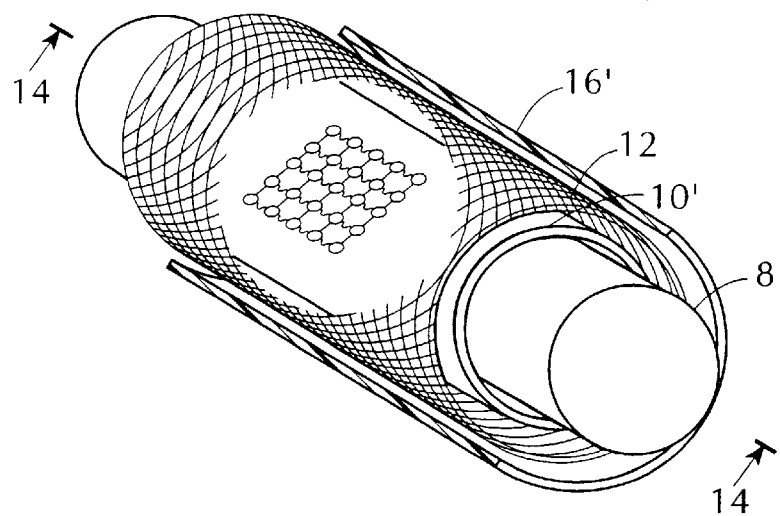
Figure 11:
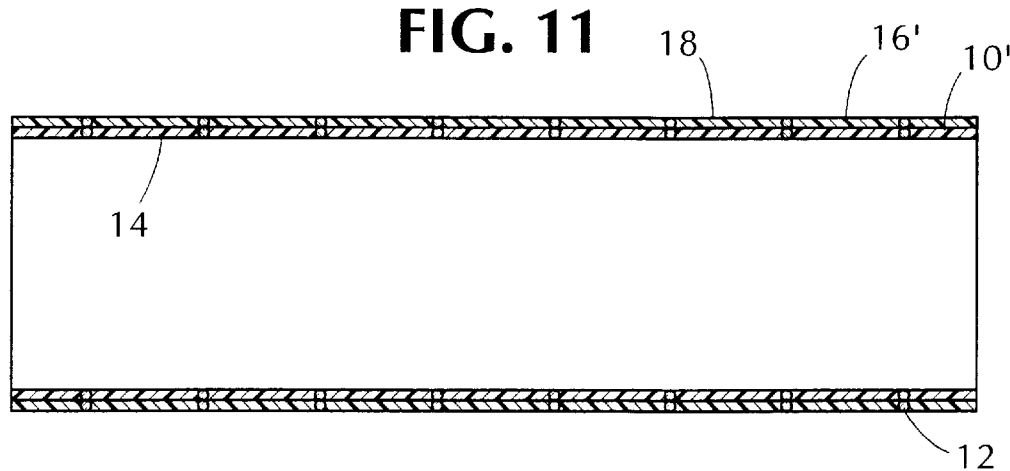
Figure 12:
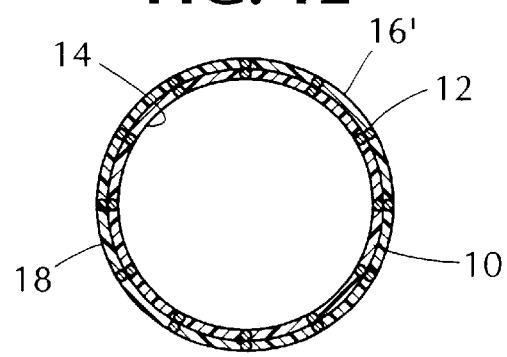

Referring now to FIGS. 1–3, the present invention relates to a flexible and generally cylindrical expandable stent-graft 20 that may be made from a stent 12 and a covering of biaxially oriented, expanded polytetrafluoroethylene material 3. The biaxially oriented, expanded polytetrafluoroethylene material 3 has a microstructure comprised of nodules 2 and fibrils 4, 4' and inter-nodule distances α, α', θ, θ'.

The term biaxial, expanded polytetrafluoroethylene material as used herein means a biaxially oriented expanded polytetrafluoroethylene material. The term uniaxial, expanded polytetrafluoroethylene material as used herein means a uniaxially oriented expanded polytetrafluoroethylene material. The average longitudinal inter-nodule distance of either uniaxial or biaxial expanded polytetrafluoroethylene may be between about 5 and about 150 microns in the free state, preferably between about 20 and about 60 microns in the free state. The longitudinal orientation and resulting longitudinal inter-nodule distances are based on the orientation when the expanded polytetrafluoroethylene is placed on a stent, such that the longitudinal orientation of the stent and expanded polytetrafluoroethylene substantially correspond with one another. The expanded polytetrafluoroethylene is in a free state when no force is applied thereto.

A preferred embodiment of the expandable stent-graft 20 of the present invention may be designed so that its expanded polytetrafluoroethylene covering 10' is associated with the expansion or compression of the stent 12 (FIG. 13), as the expandable stent-graft 20 is inserted in a delivery catheter or deployed into a body lumen. The expandable stent-graft 20 is intended for repair and support of body vessel walls.

A preferred embodiment of the expandable stent-graft 20 of the present invention may be made from a braided stent 12 such as the one described in U.S. Pat. No. 5,061,275 to Wallsten. Such a self-expanding stent is characterized in that the stent longitudinally contracts as it radially expands, and longitudinally expands as it radially contracts. Other, non-braided stents are known in the art which share this characteristic. This stent 12 may be at least partially covered, individually or in combination, with at least one layer of tube, sheet, strips or film of biaxial expanded polytetrafluoroethylene material 10 on the inside surface 14, outside surface 18, inside surface 14 and outside surface 18, or between the inside surface 14 and the outside surface 18 of the discontinuous wall of a stent 12 (FIGS. 7–13). The stent 12 and expanded polytetrafluoroethylene covering 10' may be bonded together, for instance under heat and pressure, to form the expandable stent-graft 20. Another method of bonding may include the use of another polymer such as a polyurethane or FEP which has a lower melt point.

The expandable stent-graft 20 of the present invention offers the properties of a stent 12 and the benefits of an expanded polytetrafluoroethylene covering that conforms to the compliance and distortion of the underlying stent 12. The expanded polytetrafluoroethylene microstructure (FIGS. 1–3) and it's orientation on the stent 12 (FIGS. 5–13) relate to the present invention. The expandable stent-graft 20 has characteristics that may reduce the occlusion of the lumen and improve healing of the damaged body vessels.

Another preferred embodiment of the expandable stent-graft 20 of the present invention may comprise a uniaxial, expanded polytetrafluoroethylene covering on at least part of the inside surface 14, outside surface 18, inside surface 14 and outside surface 18 or between the inside surface 14 and the outside surface 18 of the stent 12. The uniaxial, expanded polytetrafluoroethylene covering may be comprised substantially of fibrils as the nodules have been reduced substantially to zero. Other uniaxial, expanded polytetrafluoroethylene coverings may have discrete nodules so that the nodules are substantially unconnected to one another.

Another preferred embodiment of the expandable stent-graft 20 of the present invention may comprise a uniaxial, expanded polytetrafluoroethylene covering and a biaxial, expanded polytetrafluoroethylene covering 10' on at least part of the inside surface 14, outside surface 18, inside surface 14 and outside surface 18, or between the inside surface 14 and the outside surface 18 of the stent 12. The uniaxial, expanded polytetrafluoroethylene covering is comprised substantially of fibrils and is longitudinally oriented on the stent.

Figure 13:
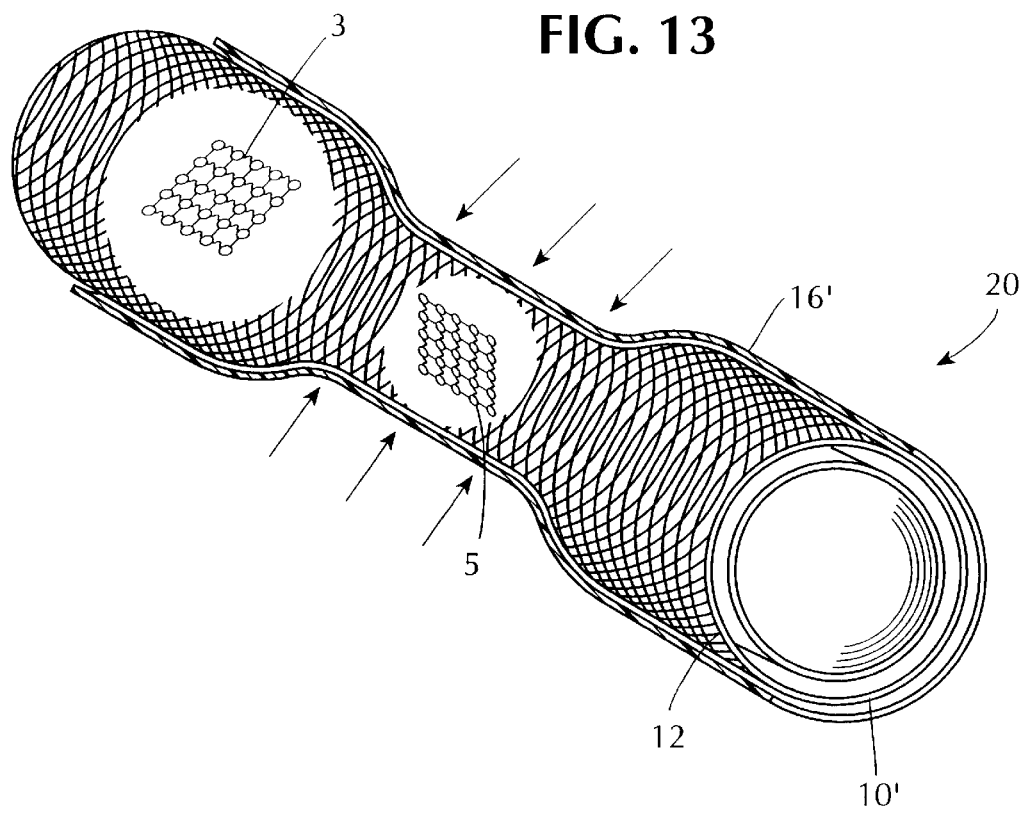
FIG. 13 depicts an illustration of the various states of the ePTFE on the stent such as when the expandable stent-graft is radially compressed or radially expanded.

In these preferred embodiments, the expanded polytetrafluoroethylene covering may correspondingly expand and contract with the stent 12. As radial and longitudinal forces are applied to the expandable stent-graft (FIG. 13), the nodule and fibril relationship may change within the biaxial expanded polytetrafluoroethylene material 10' and the fibril relationship within the uniaxial expanded polytetrafluoroethylene material and allows the covering to conform to the shape to of the stent 12. FIG. 13 illustrates an expandable stent-graft of the present invention with the end portions in at least partially radially expanded states and the mid-section in an at least partially radially contracted state.

In the preferred embodiments of the expandable stent-graft 20 of the present invention, the preferred nodule and fibril relationship of the biaxial, expanded polytetrafluoroethylene or the preferred fibril relationship of the uniaxial expanded polytetrafluoroethylene material is dependent on the dimensions of the stent 12 being covered. However, the preferred nodule and fibril relationship of the biaxial, expanded polytetrafluoroethylene in the free state or the preferred fibril relationship of the uniaxial, expanded polytetrafluoroethylene in the free state may have a circumferential fibril length ranging from about 5 microns to about 150 microns; an inter-nodule distance measured in the circumferential direction ranging from about 5 microns to about 150 microns; a longitudinal fibril length ranging from about 5 microns to about 100 microns; or an inter-nodule distance measured in the longitudinal direction ranging from about 5 microns to about 100 microns to be sufficient to offer the desired range of performance for the present invention.

The nodules 2 and fibrils 4, 4' within the biaxial, expanded polytetrafluoroethylene material may be oriented onto the stent 12 so that the longitudinal fibrils are at least substantially extended 4' to adapt to the stent 12 longitudinal expansion when the stent 12 is radially compressed; the circumferential fibrils are at least substantially folded 6' to adapt to the stent radial compression when the stent 12 is longitudinally expanded; the longitudinal fibrils are at least substantially folded 4 to adapt to the stent 12 longitudinal compression when the stent 12 is radially expanded; or the circumferential fibrils are at least substantially extended 6 to adapt to the stent radial expansion when the stent 12 is longitudinally compressed (FIGS. 6, 7, 10, and 13). The interaction of the nodules 2 and fibrils 4, 4' within the biaxial, expanded polytetrafluoroethylene material 10' allows the biaxial, expanded polytetrafluoroethylene material 10' to substantially conform to the radial and longitudinal expansion and compression of the stent 12.

The present invention also relates to a method of bonding an expanded polytetrafluoroethylene material 10, 10' onto a stent 12 so that the inter-nodule distance measured in the longitudinal direction between nodules is increased when the expandable stent-graft 20 is radially compressed; the inter-nodule distance measured in the longitudinal direction between nodules is decreased when the expandable stent-graft 20 is radially expanded; the inter-nodule distance measured in the circumferential direction between nodules 2 is increased when the expandable stent-graft 20 is longitudinally compressed; or the inter-nodule distance measured in the circumferential direction between nodules 2 is decreased when the expandable stent-graft is longitudinally expanded.

The stent 12 and expanded polytetrafluoroethylene covering 10' substantially are bonded together and substantially coextensively compress, expand or conform in shape, when radial and longitudinal forces expand or compress the expandable stent-graft 20. For example, the expandable stent-graft 20 may compress when inserted into a delivery catheter or the expandable stent-graft 20 may expand when deployed from the catheter into a body vessel.

The biaxial, expanded polytetrafluoroethylene 10, 10' or uniaxial, expanded polytetrafluoroethylene covering are not elastomers, yet, they each expand and contract with the radial or longitudinal expansion and compression forces on the expandable stent-graft 20. Also, the biaxial expanded polytetrafluoroethylene or uniaxial expanded polytetrafluoroethylene coverings may expand and compress on the expandable stent-graft 20 and have reduced folds, flaps, pillowing or kinks, thus, reducing the thrombogenic effect that may result from uneven or rough vessel surfaces. The orientation of the ePTFE and the interaction of the nodules 2 and fibrils 4, 4', 6, 6' may allow the inside surface 14 and/or the outside surface 18 to be substantially smooth in both contracted and expanded states.

Another preferred embodiment of the expandable stent-graft 20 of the present invention offers a substantially smooth covering during the radial and longitudinal compression and expansion of the expandable stent-graft 20. Radial compression and longitudinal expansion of the expandable stent-graft 20 occurs when the expandable stent-graft 20 is inserted into a catheter. Radial expansion and longitudinal compression of the expandable stent-graft 20 occurs when the expandable stent-graft 20 is deployed into various sized body vessels.

The expandable stent-graft 20 of the present invention may provide a surface that promotes increased fluid flow, reduced fluid turbulence, and overall improved compliance properties when compared to conventional covered stents. Many of the present invention characteristics are desired by medical practitioners, when repairing and healing body vessels.

When compared to an uncovered stent 12, the expanded polytetrafluoroethylene covering on the stent 12 requires little additional force to expand or contract. The biaxial, expanded polytetrafluoroethylene material 10' or uniaxial expanded polytetrafluoroethylene material substantially adapts to the radial and longitudinal expansion and compression of the stent 12. The expanded polytetrafluoroethylene covering is intended to enhance the benefits of a conventional stent 12 by adding graft capabilities, without, reducing the compliance or performance of the expandable stent-graft 20.

The expandable stent-graft 20 is generally made in the shape of a cylindrical lumen having a discontinuous wall covered with expanded polytetrafluoroethylene.

A preferred embodiment of the expandable stent-graft of the present invention has a nodule and fibril relationship in the biaxial, expanded polytetrafluoroethylene covering 10' or a fibril relationship in the uniaxial, expanded polytetrafluoroethylene covering, respectively, such that the expandable stent-graft 20 expands longitudinally up to about 300% when radially compressed as compared to it's length when in a radially expanded state.

Another preferred embodiment of the expandable stent-graft 20 of the present invention has a nodule and fibril relationship in the biaxial, expanded polytetrafluoroethylene covering 10' or a fibril relationship in the uniaxial, expanded polytetrafluoroethylene covering such that the expandable stent-graft 20 expands radially up to about 1000% of its fully radially compressed diameter measurement.

Another preferred embodiments of the expandable stent-graft 20 of the present invention may comprise at least one partial layer of biaxial, expanded polytetrafluoroethylene or a uniaxial 10', expanded polytetrafluoroethylene or a combination of a biaxial, expanded polytetrafluoroethylene 10' and a uniaxial, expanded polytetrafluoroethylene material. The uniaxial, expanded polytetrafluoroethylene material has a fibril relationship and is comprised substantially of fibrils as the nodules 2 have been reduced essentially to nearly zero. Each layer of biaxial or uniaxial, expanded polytetrafluoroethylene material may have a thickness ranging from about 10 to about 500 microns and may be made from tube, sheet, film or a plurality of strips disposed on the inner surface 14 of the discontinuous wall, outer surface 18 of the discontinuous wall, both the inner surface 14 and outer surface 18 of the discontinuous wall of the stent or between the inner surface 14 and outer surface 18 of the discontinuous wall of the stent 12 including the voids between the mesh of the walls. The discontinuous wall and the expanded polytetrafluoroethylene material are bonded at a temperature range of about 340° C. to about 390° C.

In a further embodiment of the expandable stent-graft 20 of the present invention, the discontinuous wall of the stent 12 may be coated with expanded polytetrafluoroethylene, polytetrafluoroethylene or both expanded polytetrafluoroethylene and polytetrafluoroethylene on at least part of its surface.

The preferred embodiments of the expandable stent-graft 20 of the present invention, may be produced by the method of placing a biaxial expanded polytetrafluoroethylene material 10 on a mandrel 8 in an at least partially expanded state, and then longitudinally compressing the biaxial, expanded polytetrafluoroethylene material 10 while it is positioned on the mandrel 8 so that the longitudinal fibrils are at least substantially folded 4 and the circumferential fibrils are at least substantially extended 6 or so that the inter-nodule distance measured in the longitudinal direction between nodules 2 is decreased and the inter-nodule distance measured in the circumferential direction between nodules 2 is increased. A stent 12 having an inside diameter greater than the combined diameter of the expanded polytetrafluoroethylene material and the mandrel 8 is then placed onto the outer surface of the expanded polytetrafluoroethylene material. Contact is then maintained between the stent and the expanded polytetrafluoroethylene material while the covering and the stent are heated to a temperature ranging from about 340° C. to about 390° C. for a time ranging from about 1 minute to about 15 minutes to bond the expanded polytetrafluoroethylene material to the discontinuous wall of the stent. The expandable stent-graft is then cooled and removed from the mandrel.

Additionally, the preferred embodiments of the expandable stent-graft of the present invention may also be produced by the method of placing a biaxial expanded polytetrafluoroethylene material on a mandrel and then longitudinally expanding or stretching the biaxial, expanded polytetrafluoroethylene material while it is positioned on the mandrel so that the longitudinal fibrils are at least substantially extended and the circumferential fibrils are at least substantially folded. Also, the inter-nodule distance measured in the longitudinal direction between nodules 2 may be increased and the inter-nodule distance measured in the circumferential direction between nodules 2 may be decreased. A stent having a diameter greater than the combined diameter of the expanded polytetrafluoroethylene material and the mandrel is then placed onto the outer surface of the expanded polytetrafluoroethylene material. The expandable stent-graft is radially compressed and contact is then maintained between the stent and the expanded polytetrafluoroethylene material while the covering and the stent are heated to a temperature ranging from about 340° C. to about 390° C. for a time ranging from about 1 minute to about 15 minutes to bond the expanded polytetrafluoroethylene material to the discontinuous wall of the stent. The expandable stent-graft is then cooled and removed from the mandrel.

The preferred embodiment of the expandable stent-graft of the present invention may also be produced by longitudinally compressing the expanded polytetrafluoroethylene material, prior to the step of placing the expanded polytetrafluoroethylene material on the mandrel.

The preferred embodiment of the expandable stent-graft of the present invention may also be produced by longitudinally expanding or stretching the expanded polytetrafluoroethylene material prior to the step of placing the expanded polytetrafluoroethylene material on the mandrel. An expanded polytetrafluoroethylene tape can be diagonally wound under tension about an at least partially expanded stent. Additional compressible and expandable objects of varying size, shape, compliance or dimension may also be able to take advantage of the expanded polytetrafluoroethylene coverings.

This invention has been described herein in considerable detail to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and procedures, can be accomplished without departing from the scope of the invention itself. Therefore, the spirit and scope of the claims should not be limited to the description of the preferred versions contained herein.

What is claimed is:

1. An expandable prosthesis comprising:
   (a) a discontinuous wall defining a lumen adapted to assume a longitudinally contracted position and a longitudinally expanded position; and
   (b) at least one layer of expanded polytetrafluoroethylene defining spaced-apart nodes interconnected by longitudinally directed fibrils, said nodes having a first average longitudinal inter-nodule distance in a free state, the layer of polytetrafluoroethylene affixed to the wall such that it has a second average longitudinal inter-nodule distance when the wall is in the longitudinally contracted position, the second average longitudinal inter-nodule distance being less than the first average longitudinal inter-nodule distance, said longitudinally directed fibrils being extended in said free state and being folded in said longitudinally contracted state.

2. The prosthesis of claim 1 wherein the layer of expanded polytetrafluoroethylene has (i) an average longitudinal inter-nodule distance of between about 0 and about 50 microns when the wall is in the longitudinally contracted position, and (ii) an average longitudinal inter-nodule distance of between about 50 and about 150 microns when the wall is in the longitudinally expanded position.

3. The prosthesis of claim 2 wherein the layer of expanded polytetrafluoroethylene has (i) an average longitudinal inter-nodule distance when the wall is in the longitudinally contracted position of between about 5 and about 45 microns.

4. The prosthesis of claim 3 wherein the layer of expanded polytetrafluoroethylene has (i) an average longitudinal inter-nodule distance when the wall is in the longitudinally contracted position of between about 20 and about 30 microns.

5. The prosthesis of claim 2 wherein the layer of expanded polytetrafluoroethylene has (ii) an average longitudinal inter-nodule distance when the wall is in the longitudinally expanded position of between about 60 and about 140 microns.

6. The prosthesis of claim 5 wherein the layer of expanded polytetrafluoroethylene has (ii) an average longitudinal inter-nodule distance when the wall is in the longitudinally expanded position of between about 80 and about 120 microns.

7. An expandable prosthesis comprising:
   (a) a discontinuous wall defining a lumen adapted to assume a radially contracted position and a radially expanded position; and
   (b) at least one tubular layer of an expanded polytetrafluoroethylene defining spaced-apart nodes interconnected by circumferentially directed fibrils, said nodes having a first average circumferential inter-nodule distance in a free state, the layer of polytetrafluoroethylene affixed to the wall such that it has a second average circumferential inter-nodule distance when the wall is in the radially contracted state, the second average circumferential inter-nodule distance being less than the first average circumferential inter-nodule distance said fibrils being circumferentially extended in said free state and being folded in said radially contracted state.

8. The prosthesis of claim 7 wherein the tubular layer of expanded polytetrafluoroethylene has (i) an average circumferential inter-nodule distance of between about 0 and about 75 microns when the wall is in the radially contracted position, and (ii) an average circumferential inter-nodule distance of between about 75 and about 150 microns when the wall is in the radially expanded position.

9. The prosthesis of claim 8 wherein the tubular layer of expanded polytetrafluoroethylene has (i) an average circumferential inter-nodule distance of between about 5 and about 70 microns when the wall is in the radially contracted position.

10. The prosthesis of claim 9 wherein the tubular layer of expanded polytetrafluoroethylene has (i) an average circumferential inter-nodule distance of between about 20 and about 50 microns when the wall is in the radially contracted position.

11. The prosthesis of claim 8 wherein the tubular layer of expanded polytetrafluoroethylene has (ii) an average circumferential inter-nodule distance of between about 80 and about 140 microns when the wall is in the radially expanded position.

12. The prosthesis of claim 11 wherein the tubular layer of expanded polytetrafluoroethylene has (ii) an average circumferential inter-nodule distance of between about 80 and about 120 microns when the wall is in the radially expanded position.

13. An expandable prosthesis comprising:
   (a) a discontinuous wall generally defining a lumen adapted to assume a longitudinally expanded position and a longitudinally contracted position; and
   (b) at least one layer of expanded polytetrafluoroethylene defining spaced apart nodes interconnected by longitudinally directed fibrils, said nodes having a first average longitudinal inter-nodule distance in a free state, the layer of polytetrafluoroethylene affixed to the wall such that the polytetrafluoroethylene has a second average longitudinal inter-nodule distance between 0 and 99 percent of the first average longitudinal inter-nodule distance when the wall is in the longitudinally contracted position said second average longitudinal inter-nodule distance being defined by said longitudinally directed fibrils being folded.

14. The prosthesis of claim 13 wherein the second average longitudinal inter-nodule distance is between about 20 and about 50 percent of the first average longitudinal inter-nodule distance when the wall is in the longitudinally contracted position.

15. An expandable prothesis comprising:
   (a) a discontinuous wall generally defining a lumen adapted to assume a radially expanded position and a radially contracted position; and
   (b) at least one layer of expanded polytetrafluoroethylene defining spaced apart nodes interconnected by circumferentially directed fibrils, said nodes having a first average circumferential inter-nodule distance in a free state, the layer of polytetrafluoroethylene affixed to the wall such that the polytetrafluoroethylene has a second average circumferential inter-nodule distance less than about 50 percent of the first average circumferential inter-nodule distance when the wall is in the radially contracted position said second average circumferential inter-nodule distance being defined by said circumferentially directed fibrils being folded.

16. The prosthesis of claim 15 wherein the second average circumferential inter-nodule distance is less than about 25 percent of the first average circumferential inter-nodule distance when the wall is in the radially contracted position.

17. An expandable prosthesis comprising:
   (a) a discontinuous wall defining a lumen adapted to assume a radially expanded position and a radially contracted position; and
   (b) at least one layer of expanded polytetrafluoroethylene defining spaced apart nodes interconnected by longitudinally and circumferentially directed fibrils, said nodes having a first average longitudinal inter-nodule distance and a first average circumferential inter-nodule distance in a free state, the layer of the polytetrafluoroethylene affixed to the wall such that the polytetrafluoroethylene has a second average longitudinal inter-nodule distance between 0 and 99 percent of the first average longitudinal inter-nodule distance when the wall is in the radially expanded position and a second average circumferential inter-nodule distance less than about 50 percent of the first average circumferential inter-nodule distance when the wall is in the radially contracted position said second average longitudinal and circumferentially inter-nodule distance being defined by said fibrils being folded.

18. The prosthesis of claim 17 wherein the second average longitudinal inter-nodule distance is between about 20 and about 50 percent of the first average longitudinal inter-nodule distance, and the second average circumferential inter-nodule distance is less than about 25 percent of the first average circumferential inter-nodule distance.

* * * * *